United States Patent
Bian et al.

(10) Patent No.: US 9,655,913 B2
(45) Date of Patent: May 23, 2017

(54) ANTI-ESOPHAGEAL CANCER COMPOUND AND METHOD OF USE THEREOF

(71) Applicants: Hong Kong Baptist University, Kowloon (HK); Changshu HKBU Technology Company Limited, Jiangsu (CN)

(72) Inventors: Zhaoxiang Bian, Kowloon (HK); Huaixue Mu, Kowloon (HK); Chengyuan Lin, Kowloon (HK); Jinjin Wang, Kowloon (HK); Zhijun Yang, Kowloon (HK); Aiping Lu, Kowloon (HK); Albert Sun Chi Chan, Kowloon (HK)

(73) Assignees: Hong Kong Baptist University, Hong Kong (HK); Changshu HKBU Technology Company Limited (CN)

( * ) Notice: Subject to any disclaimer, the term of this patent is extended or adjusted under 35 U.S.C. 154(b) by 0 days.

(21) Appl. No.: 15/190,367

(22) Filed: Jun. 23, 2016

(65) Prior Publication Data
US 2017/0014438 A1 Jan. 19, 2017

Related U.S. Application Data

(60) Provisional application No. 62/183,729, filed on Jun. 23, 2015.

(51) Int. Cl.
| | | |
|---|---|---|
| A61K 31/7048 | (2006.01) | |
| A61K 36/888 | (2006.01) | |
| A61K 31/09 | (2006.01) | |
| A61K 31/341 | (2006.01) | |
| A61K 31/34 | (2006.01) | |
| A61K 9/00 | (2006.01) | |
| A61K 31/353 | (2006.01) | |

(52) U.S. Cl.
CPC ........ *A61K 31/7048* (2013.01); *A61K 9/0019* (2013.01); *A61K 9/0053* (2013.01); *A61K 31/09* (2013.01); *A61K 31/34* (2013.01); *A61K 31/341* (2013.01); *A61K 31/353* (2013.01); *A61K 36/888* (2013.01)

(58) Field of Classification Search
None
See application file for complete search history.

(56) References Cited

FOREIGN PATENT DOCUMENTS

CN 102863376 * 1/2013

OTHER PUBLICATIONS

Tundis et al., Zeitschrift fuer Naturforschung, C: Journal of Biosciences, 63(5/6), 2008, pp. 347-354.*
Reagan-Shaw et al, "Dose translation from animal to human studies revisited," The FASEB Journal, Mar. 2007, pp. 659-661, vol. 22 Mar. 2007, the Federation of American Societies for Experimental Biology, Bethesda, Maryland, United States, 3 pages.

* cited by examiner

*Primary Examiner* — Traviss C McIntosh, III
(74) *Attorney, Agent, or Firm* — Ware, Fressola, Maguire & Barber LLP

(57) ABSTRACT

The present invention relates to the bioactive components with the anti-proliferative property. In particular, the invention relates to one flavonol compound isolated from the root of *Lasia spinosa* Linn. Thwait or chemically synthesized and its specific anticancer/antitumor activity. This invention has a specific application in treating human esophageal cancer.

4 Claims, 6 Drawing Sheets

ANTI-ESOPHAGEAL CANCER COMPOUND AND METHOD OF USE THEREOF

CROSS-REFERENCE TO RELATED APPLICATIONS

This application claims the benefit of U.S. Provisional Patent Application Ser. No. 62/183,728 filed Jun. 23, 2015; 62/183,729 filed Jun. 23, 2015 and 62/183,726 filed Jun. 23, 2015; the disclosures of which are incorporated herein by reference in their entirety.

FIELD OF INVENTION

The present invention relates to a method for treating cancer using an anti-cancer compound. More particularly, it relates to an anti-esophageal-cancer compound that can be isolated from *Lasia spinosa* Linn. Thwait or chemically synthesized. This invention has a specific application in treating human esophageal cancer.

BACKGROUND OF INVENTION

*Lasia spinosa* Linn. Thwait (Araceae, subfamily Lasioideas) is a herb with an underground rhizome, native to Thailand, Malaysia, Indian and southwest China. It is commonly used in many Asian countries as an anti-rheumatic, dyspepsia and chronic gastritis remedy. In this invention, the crude extract of root of *Lasia spinosa* Linn. Thwait was evaluated and one flavonol with significant anti-cancer migration activity was identified from the active n-butyl alcohol extract. Thus, the extract can be developed as an anti-cancer drug against esophageal cancer.

Citation or identification of any reference in this section or any other section of this application shall not be construed as an admission that such reference is available as prior art for the present application.

SUMMARY OF INVENTION

Accordingly, the objective of this invention is to provide a natural compound from a natural source that exhibits potent anti-inflammatory and anti-cancer effects, and thus, the natural compound may be developed as an anticancer drug.

In accordance with one aspect of the present invention, there is provided a method for inhibiting the growth of esophageal tumors in a subject in need thereof by administering to said subject a composition comprising an effective amount of a compound comprising a structural unit of

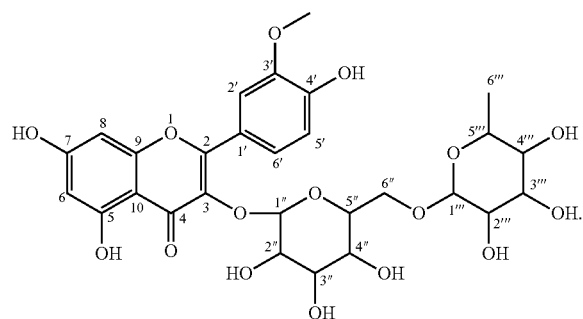

In a first embodiment of one aspect of the present invention, the effective amount is no more than 2.43 mg/kg/day.

In a second embodiment of one aspect of the present invention, the subject in need thereof is a human.

In a third embodiment of one aspect of the present invention, the compound is administered via intraperitoneal injection.

In a fourth embodiment of one aspect of the present invention, the composition comprising a compound of $C_{28}H_{32}O_{16}$.

In a fifth embodiment of one aspect of the present invention, the compound is extracted from roots of *Lasia spinosa* (L.) Thwait.

In a sixth embodiment of one aspect of the present invention, the compound is extracted from roots of *Lasia spinosa* (L.) Thwait.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

The present invention is not to be limited in scope by any of the specific embodiments described herein. The following embodiments are presented for exemplification only.

Figure 1:
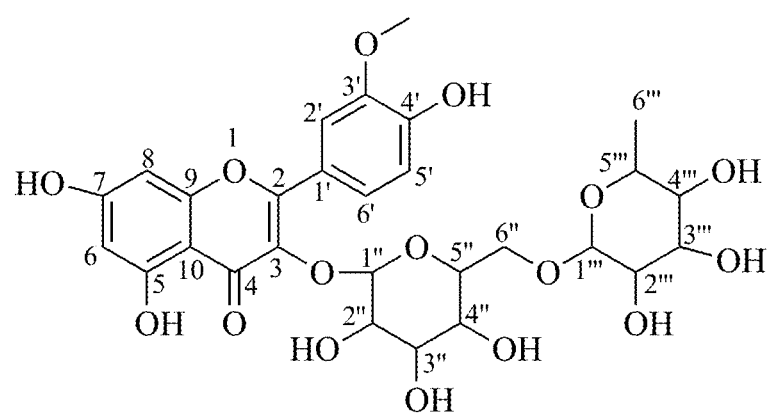
FIG. 1 shows the structure of compound 1.

*Lasia spinosa* Linn. Thwait belongs to the family of Araceae, and it was widely used in many Asian countries to treat a wide range of diseases. In this invention, the bioactive components with the anti-proliferative property were identified. Compound 1 (FIG. 1) was identified by 1D and 2D spectrum and possessed the most potent effects, with significant suppressive effect on migration of KYSE-150 cells. Furthermore, compound 1 significantly inhibited the tumor growth in the nude mice implanted with KYSE-150 cells. Thus, compound 1 isolated from the root of *Lasia spinosa* Linn. Thwait might be used as a potential antitumor drug.

Experimental Procedures

MTT (3-[4, 5-dimethylthiazol-2-yl]-2, 5-diphenyltetrazolium bromide) and DMSO (dimethyl sulfoxide) and all chemicals used were of HPLC grade from Sigma Chemical Co. (St. Louis, Mo., USA). $^1$H NMR and $^{13}$C NMR spectra were recorded on Bruker-Avance 400 MHz spectrometer. $CD_3OD$ was used as a solvent. Chemical shifts (δ) were reported in ppm with tetramethylsilane as an internal standard, and J values were given in Hz. High resolution mass spectra (HRMS) were performed on a VG Autospec-3000 spectrometer. Column chromatography was performed with the preparative HPLC. A waters 2535 Series machine equipped with Alltech Alltima-$C_{18}$ (4.6×250 mm, 5 µm) was used for HPLC analysis, and the preparative Alltech Alltima-$C_{18}$ (10×250 mm, 5 µm) was used in sample preparation.

Extraction, Isolation and Identification

Air-dried roots of *Lasia spinosa* (L.) Thwait (500 g) were extracted with 75% EtOH under reflux (3×2 L). A residue (yield 4.6%) was dissolved and suspended in 100 mL of water prior to be partitioned by different solvents. Different layers were weighted as followed: hexane extract (0.3 g, 0.06%), ethyl acetate extract (3.5 g, 0.7%), n-butanol extract (3.5 g, 0.7%), aqueous extract (12.1 g, 2.4%). All extracts were stored at −20° C. before use. The most effective fraction (n-butyl alcohol extract) was subjected to the semi-preparative column so as to obtain compound 1 (15.3 mg).

Column chromatographic separation of the n-butanol layer from the ethanol extract of the roots of *Lasia spinosa* (L.) Thwait afforded one flavonol 1. The structure of the compound was in shown in FIG. 1.

Compound 1: $C_{28}H_{32}O_{16}$, [M+H]$^+$: 625.1773 (Calcd. for 625.1769). $^1$H NMR (400 MHz, $CD_3OD$): δ7.94 (1H, d, J=1.6 Hz, H-2'), 7.62 (1H, dd, J=1.6, 8.4 Hz, H-6'), 6.91 (1H, d, J=8.4 Hz, H-5'), 6.40 (1H, m, H-8), 6.20 (1H, d, J=1.2 Hz, H-6), 5.23 (1H, d, J=7.2 Hz, H-1″), 4.53 (1H, m, H-1‴), 3.94 (3H, s, 3'-OMe), 3.86-3.80 (2H, m, H-6″), 3.61 (1H, d, J=2 Hz, H-2‴), 3.49 (1H, J=3.6 Hz, H-3‴), 3.78-3.46 (2H, m, H-2″, 5″), 3.44-3.42 (1H, m, H-5‴), 3.40 (1H, dd, J=3.2, 6.4 Hz, H-3″), 1.10 (3H, d, J=6.4 Hz, H-2'); $^{13}$C NMR (100 MHz, $CD_3OD$): 177.89 (s, C-4), 164.93 (s, C-7), 161.58 (s, C-5), 157.43 (s, C-2), 157.11 (s, C-9), 149.45 (s, C-3'), 146.91 (s, C-4'), 134.07 (s, C-3), 122.59 (d, C-6'), 121.60 (s, C-1'), 114.70 (d, C-5'), 113.17 (d, C-2'), 104.21 (d, C-10), 103.07 (d, C-1″), 101.11 (d, C-1‴), 98.66 (d, C-6), 93.59 (d, C-8), 76.78 (d, C-5″), 75.96 (d, C-3″), 74.51 (d, C-2″), 72.44 (d, C-4″), 70.88 (d, C-3‴), 70.67 (d, C-2‴), 70.22 (d, C-4‴), 68.37 (d, C-5‴), 67.13 (t, C-6″), 55.37 (q, 3'-OMe), 16.47 (q, H-6‴).

Cytotoxicity Assay

In this invention, compound 1 was dissolved in dimethyl sulfoxide (DMSO) to make stock solutions and further diluted in culture medium for this experiment. Human esophagus carcinoma cancer cell lines (KYSE-70, KYSE-150, KYSE-450 and KYSE-520) were cultured in RPMI 1640 or DMEM medium, containing 10% fetal bovine serum and 1% antibiotics (Penicillin and strep). The cell lines were cultured at 37° C. in a humidified environment containing 5% $CO_2$. A standard colorimetric MTT assay was used to determine the cell viability. Cells were seeded in a 96-well plate (3×10$^3$ cells/well) and allowed to attach to the plate overnight. After the recovery, cells were treated with various concentrations of compound 1 or the crude extract (1.56, 3.125, 6.25, 12.5, 25, 50 µg/mL) for 48 hours. Then, 20 µL of MTT (5 mg/mL stock in PBS) per well was added into the medium (200 µL) and incubated for 4 hours at 37° C. Finally, the culture medium was removed and 200 µL of DMSO were added. Absorbance of the solution was measured using a microplate reader spectrophotometer (Bio-Rad Laboratories, Inc., Hercules, Calif.) at a wavelength of 570 nm.

Wound Healing Assay

Cells were seeded in 12 wells plate at 30% confluence by scoring with a sterile plastic tip (1 mL), then washed several times with medium to remove cell debris and then incubated in the conditioned medium in the absence or presence of compound 1 at 50 µg/mL for various periods of time up to 72 hours. Cell migration into the wound surface was monitored by Olympus IX71 microscopy and digitally photographed.

Animal Experiment

Six to eight-week-old female Balb/c nude weighing between 16-20 g were bred in 12 h day/night cycle environment with free access to food and water. 2×10$^6$ KYSE-150 cells per 200 mL saline were injected subcutaneously into the flanks of the mice. When the tumor volume reached about 100 mm$^3$, the mice were randomly divided into three groups (n=5) as followed: (i) a control group: administered with saline; (ii) a low dosage group: administered with compound 1 at 15 mg/kg/day by intraperitoneal injection; (iii) a high dosage group, administered with compound 1 at 30 mg/kg/day by intraperitoneal injection. Tumor volumes were calculated with calipers every two days according to the formula: Volume=(width)$^2$×length/2. After 12 days observation, mice were killed to remove the tumor. Then the samples were fixed in 4% paraformaldehyde and embedded in paraffin. Five-micro-meter sections were stained with hematoxylin/eosin according to a standard procedure. The protocol was approved by the committee for Care of Laboratory Animals in the School of Chinese Medicine at the Hong Kong Baptist University.

Human equivalent dosage is converted from the mouse dosage using the following equation: $D_{human}=D_{mouse} \times k$ (k=0.081) (Regan-Shaw et al. (2007). Disclosure thereof is incorporated herein by its entirety.) Therefore, the human equivalent dosage is in a range of 1.215 mg/kg/day to 2.43 mg/kg/day.

Discussion

It is demonstrated that different extracts of roots of *Lasia spinosa* (L.) Thwait are assayed in vitro for their anti-proliferative activities against MDA-MB-231, NCI-N87, Hep-G2, KYSE-70, KYSE-150 and HEKSE-3 cells through the MTT method as shown in Table 1. N-butanol layer of roots of *Lasia spinosa* (L.) Thwait shows the most effective in anti-proliferative effects.

TABLE 1

Cytotoxicity of all extracts against cancer cell lines[a]

| Cell lines | PE ext. | EtOAc ext. | BuOH ext. | H$_2$O ext. |
|---|---|---|---|---|
| MDA-MB-231 | — | — | 26 | — |
| NCI-N87 | — | 27.16 | 13.64 | — |
| Hep-G2 | — | — | 21.39 | — |
| KYSE-70 | — | 50 | 24.68 | — |
| KYSE-150 | — | 50 | 32 | — |
| HKESC-3 | — | 27.16 | 27.05 | — |

[a]Results are expressed as IC$_{50}$ values in μg/mL

Figure 2:
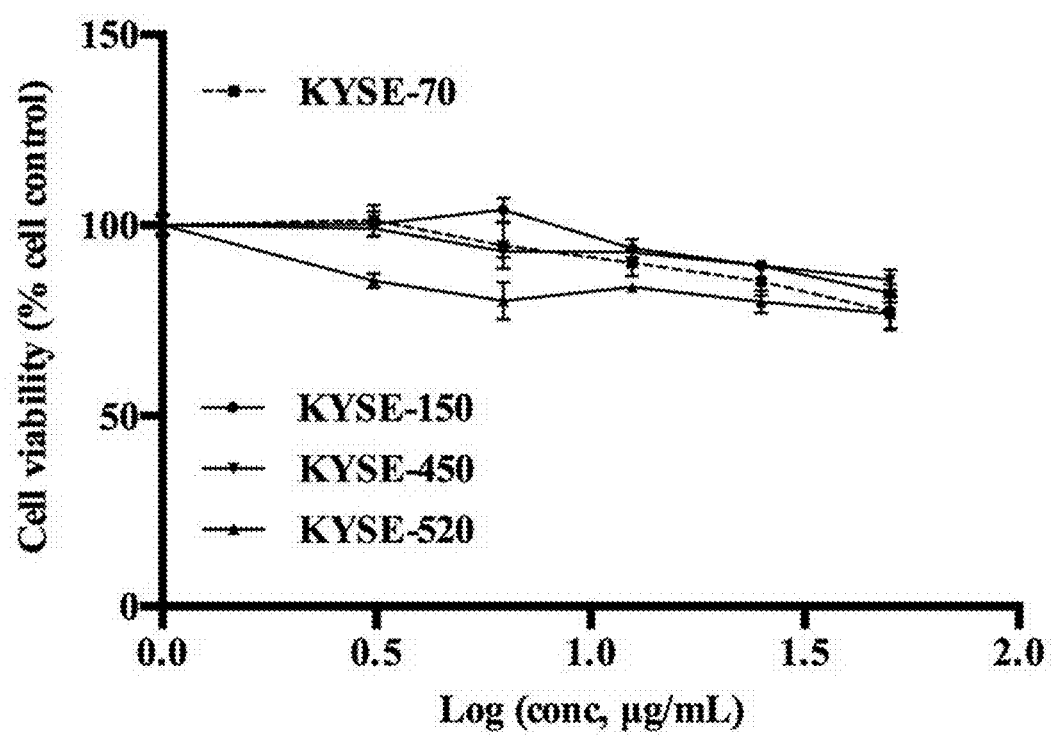
FIG. 2 shows the effect of compound 1 on the cell viability of esophagus cancer cell lines. Cells were cultured for 48 hours in the presence of compound 1 at the indicated concentrations (1.25-50 μg/mL). Each experiment was done in triplicate. Data are expressed as mean±SEM.

The cytotoxicity of compound 1 was evaluated against esophagus cancer cell lines (KYSE-70, KYSE-150, KYSE-450 and KYSE-520). As shown in FIG. 2, no cytotoxicity was observed for the compound 1 at the highest concentration of 50 μg/mL.

Figure 3:
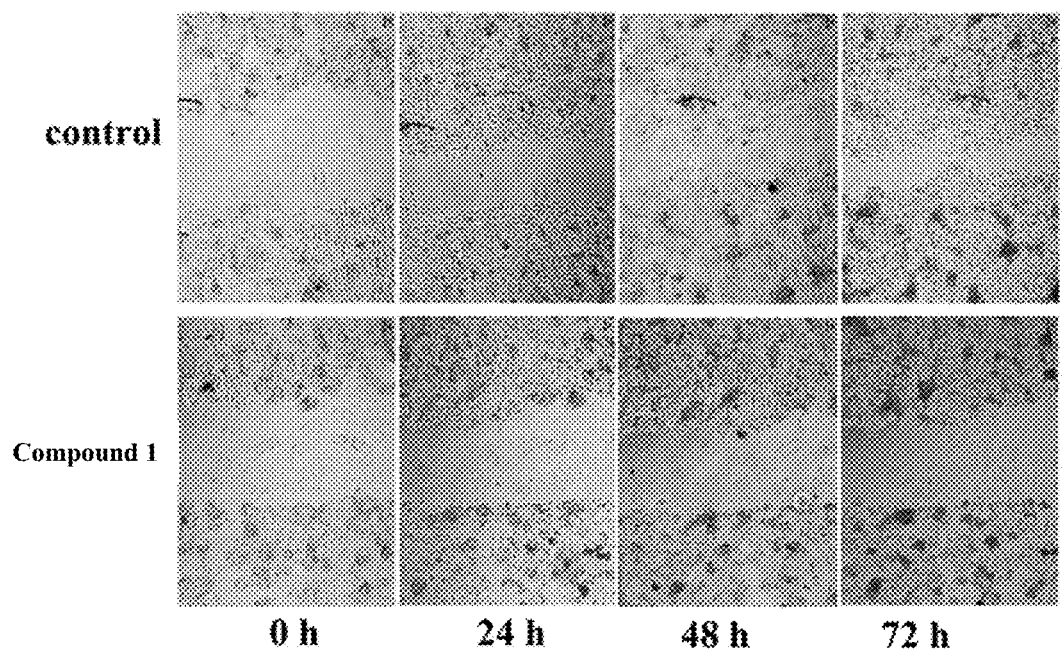
FIG. 3 shows the wound healing assay of compound 1 on human esophageal carcinoma (KYSE-150) cells. Cells were treated by compound 1 at 50 µg/mL, and at this concentration the cells viability was not altered. The original magnification is 5×.

To further examine the inhibitory effect of compound 1 on the migratory activity of cancer cell, a confluent monolayer of KYSE-150 cells was scratched to form a wound and incubated in the absence or presence of compound 1 (50 μg/mL) as compared to that of controls. After 72 hours, those treated with compound 1 significantly inhibited the cell migration compared to those in control group, as shown in FIG. 3.

Figure 4A:
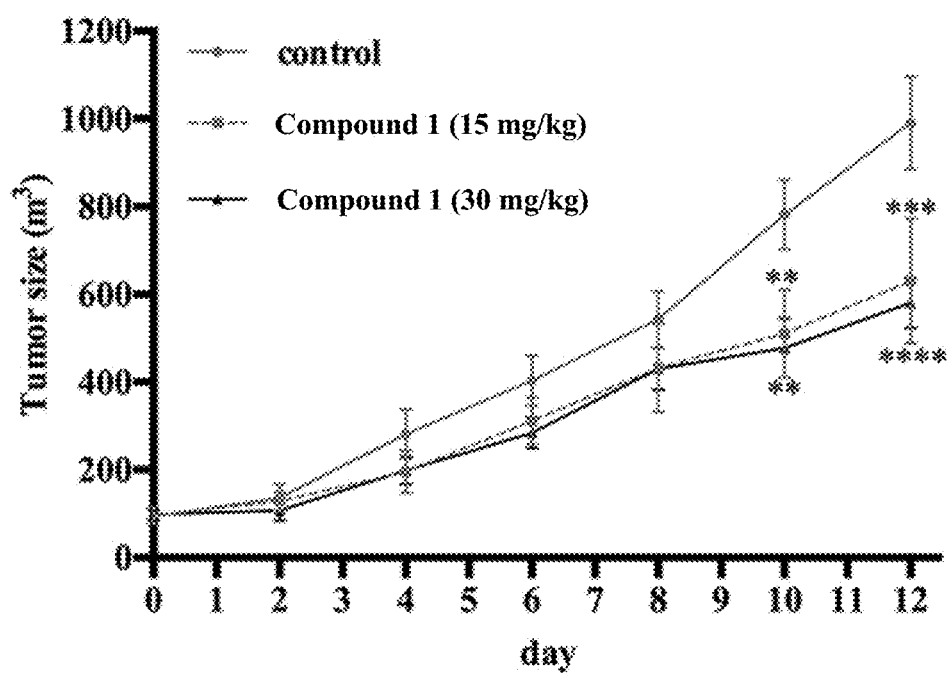
FIG. 4A shows the suppression of tumor sizes after administering compound 1 with two different dosages, namely 15 mg/kg and 30 mg/kg.
Figure 4B:
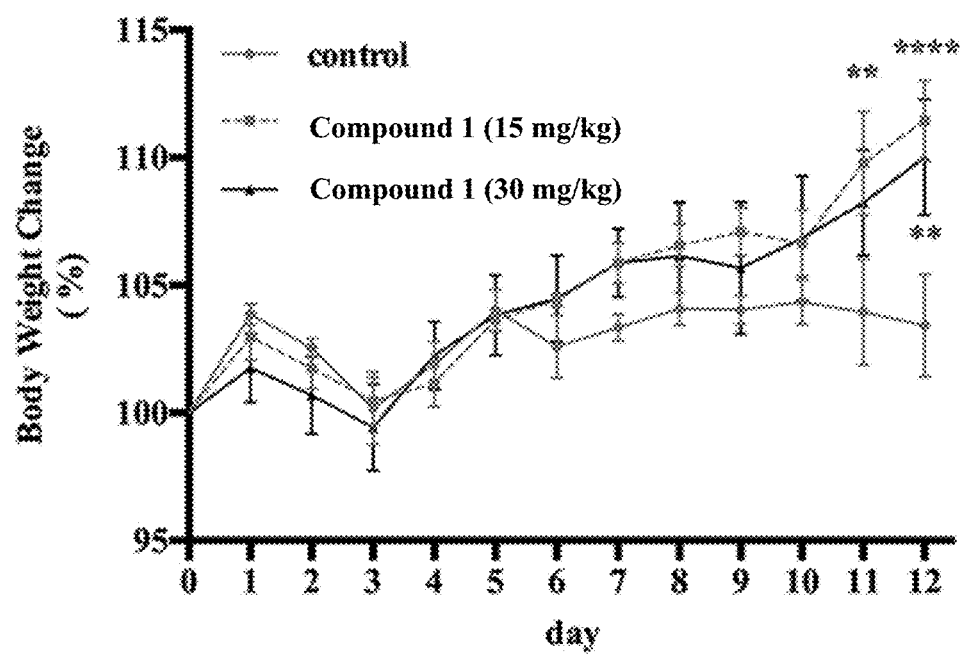
FIG. 4B shows the comparison of the change in body weight in three different groups with tumor xenografts mouse model.
Figure 4C:
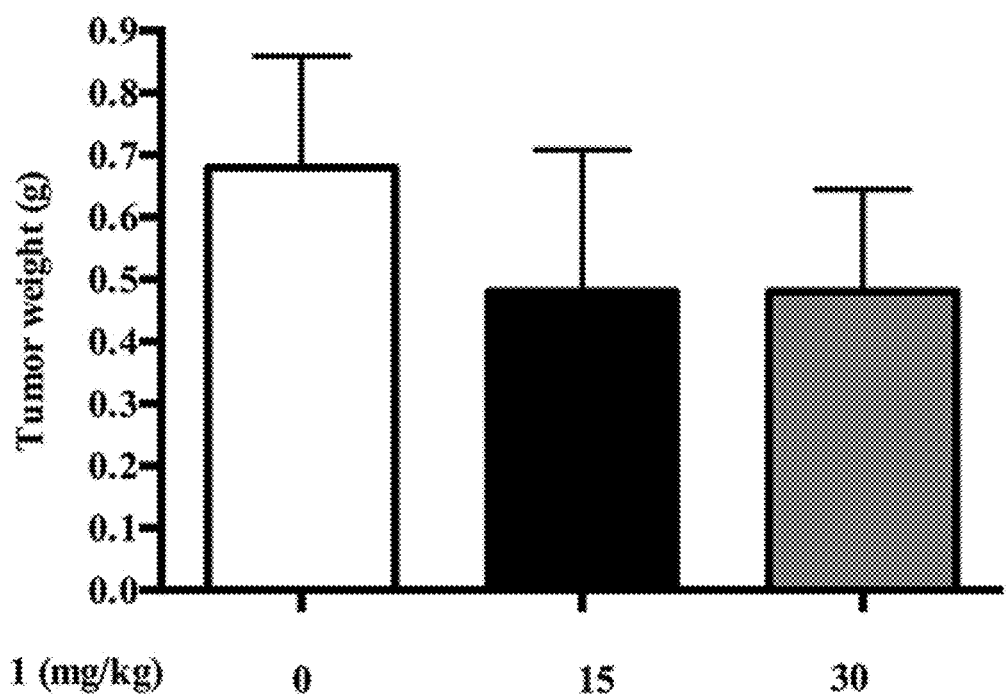
FIG. 4C shows the comparison of tumor weight in three different groups with tumor xenografts mouse model.
Figure 4D:
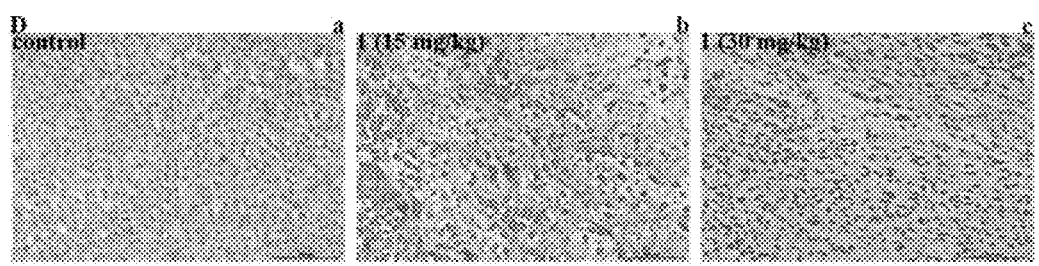
FIG. 4D shows H&E stained tumor tissues obtained from the three groups treated with saline, 15 mg/kg of compound 1, and 30 mg/kg of compound 1 respectively. (n=5, *p<0.05, p<0.01, *p<0.001, ****p<0.0001).

To assess the in vivo anti-cancer activity of compound 1, tumor xenograft mouse model was established. As shown in FIG. 4A, the tumor growth in the treatment group was significantly reduced compared to the control group. As shown in FIG. 4B, the body weight in the treatment group was significantly reduced compared to the control group. As shown in FIG. 4C, the treatment group had significantly reduced tumor weight compared to the control group. FIG. 4D shows H&E staining the therapeutic groups that were composed of massive necrotizing tissue. In contrast, there was massive viable tumor tissue with large, irregular, hyperchromatic nuclei in the control group. The results implied that compound 1 had attenuated the tumor growth in vivo.

Industrial Applicability

This invention provides an anti-cancer *Lasia spinosa* Linn. Thwait and shows its anti-esophageal cancer effects. In summary, *Lasia spinosa* Linn. Thwait can be further developed as an anticancer drug against esophageal cancer.

We claim:

1. A method for inhibiting the growth of an esophageal tumor in a subject in need thereof by administering to said subject a composition comprising an effective amount of a compound comprising a structural unit of

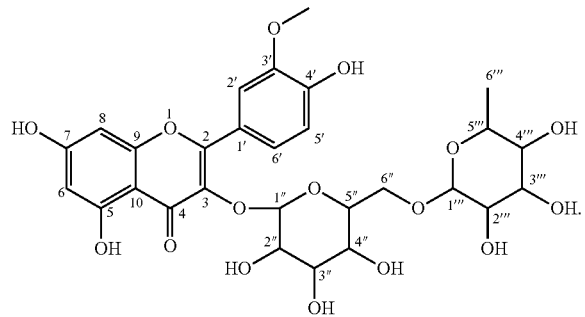

2. The method according to claim 1 wherein the effective amount of the compound is no more than 2.43 mg/kg/day.

3. The method according to claim 1 wherein the subject in need thereof is a human.

4. The method according to claim 1 wherein the compound is administered via intraperitoneal injection.

* * * * *